United States Patent [19]

Mikkelsen

[11] Plant 4,203

[45] Jan. 31, 1978

[54] IMPATIENS PLANT

[75] Inventor: James C. Mikkelsen, Ashtabula, Ohio

[73] Assignee: Mikkelsens, Inc., Ashtabula, Ohio

[21] Appl. No.: 764,024

[22] Filed: Jan. 31, 1977

[51] Int. Cl.[2] ..... A01H 5/00

[52] U.S. Cl. ..... Plt./68

[58] Field of Search ..... Plt./68

*Primary Examiner*—Robert E. Bagwill
*Attorney, Agent, or Firm*—Donald D. Jeffery

[57] ABSTRACT

A novel impatiens variety having rose pink blossoms, which variety has excellent durability when grown outdoors.

1 Drawing Figure

The present invention relates to a new and distinctive cultivar of Impatiens plant, botanically known as Impatiens and known by the cultivar name Preamble. The new cultivar was developed by me through controlled breeding by crossing the unpatented cultivar 74-108-1 (Mikkelsen) (seed parent) with the unpatented cultivar 74-197-11 (Mikkelsen) (pollen parent). Asexual reproduction of terminal or stem cuttings has shown that the unique features of this new Impatiens are stabilized and are reproduced true to type in successive propagations.

The following characteristics distinguish the new cultivar from both its parent varieties and other cultivated Impatiens of this type known and used in the floriculture industry:

1. There is considerable similarity in the foliage between Preamble and Paul Revere, also a new Impatiens cultivar of mine, with Paul Revere being disclosed and claimed in my finding application Ser. No. 764,525 filed Jan. 31, 1977. However, Preamble has narrower, longer, and more elliptical foliage than Paul Revere.

2. Preamble has a greater proportion of variegation in the foliage than Paul Revere.

3. The flower color of Preamble is more rose pink than the red flower color of Paul Revere.

4. The flower shape of Preamble is more symmetrically round than the oval form of Paul Revere.

5. The individual petals of Preamble are very nearly the same size, as contrasted with those of Paul Revere which comprise three large and two smaller petals.

6. In flower tests outdoors in the summer of 1976, Preamble was by far the most durable New Guinea Impatiens hybrid tested. Flower color was outstanding, plant growth was semi-compact, and there was very little, if any, deterioration of foliage until the end of October. Foliar variegation was distinct.

7. General plant growth is ideal for pot plant culture; flowers are less durable indoors than outdoors.

8. Many compact to semi-compact New Guinea Impatiens do not produce adequate cuttings for commercial production. However, Preamble though semi-compact in growth does produce substantial amounts of side growth at each node. Normal nodal distance is 3 cm. to 5 cm.

The accompanying colored photograph illustrates the overall appearance of the new cultivar and shows the colors as true as it is reasonably possible to obtain in a colored reproduction of this type.

The following is a detailed description of my new Impatiens cultivar based on plants produced under commercial practices in the greenhouses of Mikkelsens Inc., Ashtabula, Ohio, during early September, 1976.

Color references are made to the Royal Horticultural Society Colour Chart except where general terms of ordinary dictionary significance are used.

Parentage: A controlled pollination of Mikkelsens seedling 74-108-1 as the seed parent crossed with Mikkelsens seedling 74-197-11 as the pollen parent.

Propagation:

*Type cutting.*—Terminal cuttings 2–3 cm. long.

*Time to visible rooting.*—10 days at 21° C summer, and 15 days at 20° C winter.

*Rooting habit.*—Typical for New Guinea Impatiens, rapid, very profuse in both primary and secondary roots, dendritic.

Plant description:

*Form.*—Semi-compact, short to medium height, upright, well branching herb.

*Habit of growth.*—Slow to medium rate of strong upright growth, with good to excellent branching habits.

*Foliage.*—Foliage averages between 5 and 6 leaves per node, internodal distance 3–5 cm., excellent texture, rugged, durable to outdoor exposures. Size: From 4.5 to 5 cm. wide by 9 cm. to 11 cm. long, with petiole 1 cm. to 1.5 cm. long. Shape: Highly symmetrically elliptical, apex acuminate, base cuneate, tending more to concave upward than revolute. Texture: Firm, leathery, glabrous, rugose. Margin: Entire, ciliolate. Color: Young foliage: In young plants usually solid green, near 139A, with yellow green developing quickly in tip of young foliage as plants mature. Mature foliage: Top side, outer area under low light condition, green 136A, fading to yellow green 147A; inner area, dark yellow green transcending to yellow green 151A-B. Under side: Outer area yellow green 147B, inner area cream yellow. Leaf variegation more pronounced as plant matures. Venation: pinnately, arcuate.

Flowering description:

*Flowering habit.*—Consistently one flower per leaf, opening sequentially around the whorl of leaves with up to 4–5 flowers open at one time at each whorl. Keeping quality of the flowers outdoors is superior to other cultivars in the breeding program.

*Natural flowering season.*—Flowering is indeterminate, occurring at all times of the year.

*Flower buds.*—Immature, conical to pyramidal as sepals develop. Spur emerges from backside of bottom sepal and curves to the top of the bud; later the spur hangs below in a symmetrical arch.

*Flowers borne.*—Individually on a light red/pink pedicel approximately 5 cm. long by 2 mm. at base.

*Quantity of flowers.*—Typically one per leaf, appearance of being more floriferous because of the lasting qualities of individual blooms.

*Petals.*—Top petal has scale-like sepal on underside. Shape: Generally heart shaped with indentation of the apex. Color: Top side in winter when opening is darker and more brilliant than red 43D. Color in summer is near red 54C, fading to between 54C-D; underside is 54C in winter and near 48C in summer. Number of petals: 5. Size of petals: 2 cm. × 3 cm.; flower diamter up to 5.5 cm. Curved spur is red 53-B at tip, 6 cm. long, hollow.

*Reproductive organs.*—Stamens: One in number. Anther shape: Hooded over pistil, light red in color. Pollen color: Creamy white. Pistils: Stigma shape: Flat, circular, irregular surface, translucent green in color. Style color: Green. Ovaries: One in number, size 4 mm., color green.

I claim:

1. A new and distinct cultivar of Impatiens known by the cultivar name Preamble and particularly characterized as to uniqueness by the combined characteristic of narrow, long and variegated foliage; rose pink flower color; symmetrically round flower shape, with each flower petal being nearly the same size; superior durability; produces substantial side growth thereby permitting adequate cuttings to be taken for commercial production, and by its general plant growth which is ideal for pot plant culture.

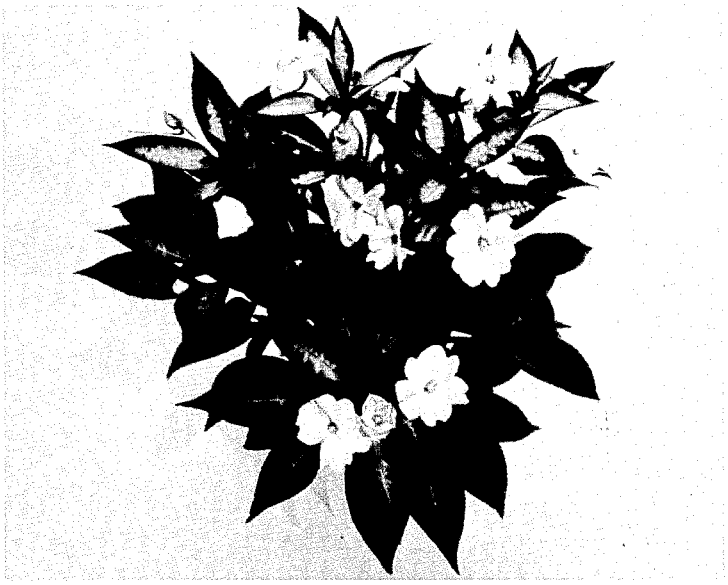

* * * * *